United States Patent [19]

Buus

[11] 3,966,952

[45] June 29, 1976

[54] ALPHA-ISOMER OF THE PALMITIC ACID ESTER OF 10-[3-(4-HYDROXYETHYL-1-PIPERAZINYL)PROPYLIDENE]-2-TRIFLUOROMETHYL THIAXANTHENE, COMPOSITIONS THEREOF AND A METHOD OF PREPARATON THEREOF AND USE THEREOF

[75] Inventor: Jorn Lasse Martin Buus, Bjaeverskov, Denmark

[73] Assignee: Kefalas A/S, Copenhagen-Valby, Denmark

[22] Filed: Dec. 4, 1974

[21] Appl. No.: 529,281

[30] Foreign Application Priority Data

Dec. 7, 1973 United Kingdom............ 56900/73

[52] U.S. Cl............................ 424/250; 260/240 R
[51] Int. Cl.² ...................................... A61K 31/493
[58] Field of Search..................... 424/250; 260/240

[56] References Cited
OTHER PUBLICATIONS

Chem. Abst., 12822–12823, vol. 59 (1963).

*Primary Examiner*—Stanley J. Friedman
*Attorney, Agent, or Firm*—Gordon W. Hueschen

[57] ABSTRACT

This invention relates to the novel alpha-isomer of the palmitic acid ester of 10-[3-(4-hydroxyethyl-1-piperazinyl) propylidene]-2-trifluoromethyl thiaxanthene, the non-toxic acid addition salts thereof, methods for the preparation of the said compound, therapeutic compositions thereof having prolonged effect, and a method of treating psychotic patients therewith.

10 Claims, No Drawings

ALPHA-ISOMER OF THE PALMITIC ACID ESTER OF 10-[3-(4-HYDROXYETHYL-1-PIPERAZINYL)-PROPYLIDENE]-2-TRIFLUOROMETHYL THIAXANTHENE, COMPOSITIONS THEREOF AND A METHOD OF PREPARATON THEREOF AND USE THEREOF

BACKGROUND OF THE INVENTION

The compound 10-[3-(4-hydroxyethyl-1-piperazinyl)propylidene]-2-trifluromethyl thiaxanthene has in the recent years, in the form of a mixture of the cis-trans isomers, proved outstanding as a neuroleptic drug in the treatment of psychotic disorders, mostly schizophrenic patients.

The compound, which in the following is called flupenthixol (pINN) for short, is effective in small doses and is preferably used in the form of acid addition salts such as the dihydrochloride in oral unit dosage forms. The daily dose normally is in the range of 1 – 3 mg three times a day. When patients are discharged from hospital on a maintenance dosis it has often been a problem to have the patients take the tablets, and the result has been a high degree of recurrences.

Recently it has been suggested to administer the most potent isomer of flupenthixol, the alpha-form, in the form of the decanoic acid ester, as oily solution for injection, and it has been shown that such solutions have a prolonged effect as compared with the unesterified alpha-isomer.

SUMMARY OF THE INVENTION

It has now surprisingly been found that the alpha-isomer of the palmitic acid ester of flupenthixol have an improved prolonged effect in comparison with the decanoic acid ester and, moreover, have a considerably lower level of cataleptic effect in rats indicating that the palmitic acid ester of alpha-flupenthixol is almost completely devoid of extrapyrimidal side effects. - Furthermore, the palmitic acid ester of alpha-flupenthixol is a crystalline substance which makes it easy to obtain in a pure state.

It is an object of the present invention to provide a new composition with improved prolonged action, few side-effects, and a method of treating psychotic patients therewith.

The compound of the present invention is the alpha-isomer of the palmitic acid ester of flupenthixol, in the following called Lu 10-040 for short, which according to one method of the invention may be prepared by reacting the alpha-isomer of flupenthixol with a reactive derivative of palmitic acid, especially an acid halide as the acid chloride.

It is a wellknown fact that the individual isomers of flupenthixol possess the desired pharmacological effects to different degrees. Thus the isomer which, as the free base, melts at 101° – 102° Centigrade (in the following called the alpha-isomer) shows by far the most pronounced neuroleptic activity, whereas the other isomer, which melts at 87° – 94° Centigrade (in the following called the beta-isomer) has much less pronounced neuroleptic activity. A mixture of the isomers of flupenthixol, which is mostly obtained when synthesizing the compound, may be separated in the individual isomers; for example by fractional crystallization from ether.

When preparing the individual isomers according to the invention is it preferred to separate the isomers of flupenthixol before the esterification process, as it is more difficult to separate the isomers after the esterification.

According to one method of the invention the alpha-isomer of flupenthixol is esterified by reaction with a reactive derivative of palmitic acid, preferably an acid halide such as the acid chloride in an inert solvent such as acetone, whereupon the palmitate is isolated in the form of the free base or in the form of a non-toxic acid addition salt, and if the palmitate is obtained as a mixture of isomers the alpha-isomer is isolated by fractional crystallization.

The non-toxic acid addition salts are preferably salts of pharmaceutically acceptable acids such as mineral acids; for example hydrochloric acid, hydrobromic acid, phosphoric acid, sulphuric acid, and the like, and organic acids such as acetic acid, oxalic acid, tataric acid, maleic acid, citric acid, methane sulphuric acid, and the like.

The following examples illustrate the method of the invention:

EXAMPLE 1

The palmitic acid ester of the isomer of 10-[3-(4-hydroxyethyl-1-piperazinyl)propylidene]-2-trifluoromethyl thiaxanthene, which melts at 101°–102° Centigrade, in the following called Lu 10-040 for short.

25 grams of the alpha-isomer of 10-[3(4-hydroxyethyl-1-piperazinyl)propylidene]-2-trifluoromethyl thiaxanthene were dissolved in 300 millilitres of dry acetone and 15 grams of the acid chloride of palmitic acid were added. The mixture was refluxed for 30 minutes, cooled, and a solution of dry hydrogen chloride in ether added to a pH of 2–3; whereupon 200 millilitres of dry ether were added. The crystals which separated out were filtered off, washed with ether and dried. The yield was 42 grams of the dihydrochloride of the palmitic acid ester of the alpha-isomer of 10-[3-(4-hydroxyethyl-1-piperazinyl)propylidene]-2-trifluoromethyl thiaxanthene, which melts at 147°–152° Centigrade.

When the dihydrochloride was treated with aqueous ammonia the free base separated out as an oil which was extracted with ether, the ether phase washed with water, dried over anhydrous magnesium sulfate and evaporated on a steam bath finally at reduced pressure 0.05 mg/Hg, whereby the free base was obtained as an oil, which on cooling solidies to a white crystalline substance which melts at 43°–45° Centigrade.

The invention further provides pharmaceutical compositions with prolonged action comprising, as active ingredient, the alpha-isomer of the palmitic acid ester of 10-[3-(4-hydroxyethyl-1-piperazinyl)propylidene]-2-trifluoromethyl thiaxanthene or one of its non-toxic acid addition salts together with a pharmaceutical carrier or excipient.

They may be administered to animals including human beings both orally, parenterally and rectally and may take the form of e.g. sterile solutions or suspensions for injection, tablets, suppositories, capsules, amd syrups. Results upon administration to human beings of the compositions of the invention have been very gratifying.

Preferably, however, the compositions are in the form of sterile solutions or suspensions for injection, and in a preferred embodiment of the invention injectable solutions may be prepared from a non-toxic injectable fat or oil, e.g. light vegetable oil, sesame oil, olive oil, arachis oil or ethyl oleate, and they may additionally contain gelling agents, e.g. aluminium stearate, to delay absorption within the body. Such oily solutions have a very prolonged activity when rejected intramuscularly, and satisfactory neuroleptic action has been produced by a single intramuscular injection of about 20–40 mg of Lu-10-040 dissolved in a light vegetable oil for as long as 2-4 weeks.

The following examples illustrate the injectable oily solutions according to the present invention:

| | | | |
|---|---|---|---|
| 1. | Lu 10-040 | 20 | grams |
| | sterile, light vegetable oil | ad 1000 | ml |
| 2. | Lu 10-040 | 30 | grams |
| | sterile sesame oil | ad 1000 | ml |
| 3. | Lu 10-040 | 40 | grams |
| | Aluminium mono stearate | 20 | grams |
| | Sterile, light vegetable oil | ad 1000 | ml |
| 4. | Lu 10-040 | 20 | grams |
| | Sterile olive oil | ad 1000 | ml |

The solutions are filled in for example ampoules each containing 1 ml solution.

The active ingredient may also be administered in the form of a suspension of micronized Lu 10-040 or a salt thereof in sterile physiologically saline.

A suitable formula for a tablet containing -2-4 mg of Lu 10-040 is as follows:

| | |
|---|---|
| Lu 10-040 | 2-4 mg |
| Potato starch | 36 mg |
| Lactose | 18 mg |
| Gelatine | 4 mg |
| Talcum | 6 mg |
| Magnesium stearate | 0.4 mg |

Any other pharmaceutical adjuvants may be used provided that they are compatible with the active ingredient, and additional compositions and dosage forms may be similar to those presently used for neuroleptics. Also combinations of Lu 10-040 as well as its pharmacologically acceptable non-toxic acid addition salts with other active ingredients especially other neuroleptics, thymoleptics or the like, fall within the scope of the present invention.

In order to evaluate the degree of prolongation of effect obtained with Lu 10-040 dissolved in light vegetable oil animal experiments were undertaken in rats and dogs to compare the duration of action with that of the decanoic acid ester of alpha-flupenthixol (in the following called Lu 5-110 for short) base in light vegetable oil.

A pharmacological criteria for "neuroleptic" action were chosen:
1. Protection against apomorphine induced vomiting in dogs
2. Protection against amphetamine induced stereotypy in rats and
3. Cataleptic reaction in rats.

All the tests included are wellknown in the pharmacological testing of neuroleptic drugs.

1. Protection against apomorphine induced vomiting in dogs:

Adult purebred Beagles of either sex were used. The method has previously been described in detail (M. Nymark et al. : "Prolonged neuroleptic effect of α-flupenthixol decanoate in oil.", Acta pharmacol. et toxicol. 1973). Briefly, the degree of protection against the emetic effect of apomorphine, expressed as multipla of the normal apomorphine threshold dose ($25\mu g/kg$ i.v.) the animal would tolerate without vomiting), was assessed at different times after subcutaneous injection of the depot-neuroleptics. Four dogs were used at each dose-level.

The results obtained showed that at a dose of 2 mg/kg s.c. Lu 10-040 yielded a higher level of protection (about twice as high) against the emetic effect of apomorphine than did the same dose of Lu 5-110. With respect to the absolute duration of protection the effect of Lu 10-040 lasted for about 18 days as compared to about 11 days for Lu 5-110.

2. Protection against amphetamine induced stereotypy in rats:

Male rats (Wistar/Af/Han/Mol (Han 67), conventional) in the weight range of 230–270 grams were pretreated with Lu 10-040 in oil (2%), 10 or 20 mg/kg s.c.

Appropriate control groups receiving injections of the vehicle were included. Each group consisted of 5-10 rats. The groups were challenged with amphetamine sulphate, 13.6 mg/kg i.v. (~10 mg/kg of amphetamine base) at different times after drug administration, however, not more than 3 times a week.

After the injection of amphetamine the animals were placed in individual cages which consisted of rectangular Perspex boxes (12 × 25 cm, height 30 cm) without bottom and lid. During the experiments the cages were placed on corrugated paper. After 55 and 65 minutes the rats were observed for stereotypy (movements of the head, compulsory chewing or licking) for one minute. The absence of stereotypy was interpreted at a drug effect.

With 19 mg/kg of Lu 10-040 and Lu 5-110 respectively the duration of effect was about 12 days for Lu 10-040 and about 7 days for Lu 5-110.

3. Cataleptic reaction (wire mesh) in rats:

Male rats (Wistar/Af/Han/Mol (Han 67), SPF, 180-220 g, were kept in Macrolon cages (Type 3); 5 rats in each cage, at a room temperature of 22°–23°C and a relative humidity of 50 ± 5%.

The animals were placed on a vertical wire mesh and were considered cataleptic when they remained immobile during a period of 15 seconds. Untreated rats climbed up and down the wire mesh.

Ten rats were used for each dose level of the drug which was injected intramuscularly (injection volume 0.25 ml/kg). At different times after drug administration the rats were checked for the presence or absence of catalepsy.

The following dosages of Lu 10-040 and Lu 5-110 were tested: 2.5, 5, 10 and 20 mg/kg. The doses 2.5, 5 and 10 mg/kg i.m. of Lu 10-040 did not induce catalepsy at all. Only the high dose, 20 mg/kg, caused catalepsy, maximal effect being 40%. In a similar experiment Lu 5-110 proved to be considerably more cataleptogenic than Lu 10-040. The almost total absence of cataleptic effect of Lu 10-040 in normally used dosages indicates that the compound does not cause extrapyrimidal symptoms, a frequent side effect of neuroleptic drugs.

I claim:
1. A compound selected from the group consisting of 1) the alpha-isomer of the palmitic acid ester of 10-[3-(4-hydroxyethyl-1-piperazinyl)propylidene]-2-trifluoromethyl thioxanthene and 2) a non-toxic acid addition salt thereof.

2. A compound of claim 1 which is the alpha-isomer of the palmitic acid ester of 10-[3-(4-hydroxyethyl-1-piperazinyl) propylidene]-2-trifluoromethyl thioxanthene.

3. A compound of claim 1 which is a non-toxic acid addition salt of the alpha-isomer of the palmitic acid ester of 10-[3-(4-hydroxyethyl-1-piperazinyl)-propylidene]-2-trifluoromethyl thioxanthene.

4. A compound of claim 1 or 3 which is the dihydrochloride of the alpha-isomer of the palmitic acid ester of 10-[3-(4-hydroxyethyl-1-piperazinyl)propylidene]-2-trifluoromehtyl thioxanthene.

5. A pharmaceutical composition in a form suitable for oral, injection, or rectal treatment of psychotic disorders comprising as active ingredient an effective neuroleptic amount of a compound selected from the group consisting of 1) the alpha-isomer of the palmitic acid ester of 10-[3-(4-hydroxyethyl-1-piperazinyl)-propylidene]-2-trifluoromethyl thioxanthene and 2) a non-toxic acid addition salt thereof, together with a pharmaceutically acceptable carrier therefor.

6. The pharmaceutical composition of claim 5, in injectable form, wherein the active ingredient is the alpha-isomer of the palmitic acid ester of 10-[3-(4-hydroxyethyl-1-piperazinyl propylidene]-2-trifluoromethyl thioxanthene.

7. The pharmaceutical composition of claim 5, wherein the active ingredient is present in an amount between about two and about forty milligrams.

8. A method for the treatment of psychotic disorders comprising the step of administering to a subject in need of such treatment an effective neuroleptic amount of a compound selected from the group consisting of (1) the alpha-isomer of the palmitic acid ester of 10-[3-(44-hydroxyethyl-1-piperazinyl)propylidene]-2-trifluoromethyl thioxanthene and (2) a non-toxic acid addition salt thereof.

9. The method of claim 8, wherein the alpha-isomer of the palmitic acid ester of 10-[3-(4-hydroxyethyl-1-piperazinyl)propylidene]-2-trifluromethyl thioxanthene is administered by parenteral injection.

10. The method of claim 8, wherein the amount of active ingredient administered is between about 2 and about 40 milligrams per unit dose.

* * * * *

UNITED STATES PATENT OFFICE
CERTIFICATE OF CORRECTION

Patent No. 3,966,952                Dated June 29, 1976

Inventor(s) Jorn Lasse Martin Buus

It is certified that error appears in the above-identified patent and that said Letters Patent are hereby corrected as shown below:

In the title:

"PREPARATON"           should read           --- PREPARATION ---

Column 6, line 13:

"(44-hydroxyethyl)"    should read           --- (4-hydroxyethyl) --

Signed and Sealed this

Twenty-sixth Day of October 1976

[SEAL]

Attest:

RUTH C. MASON
Attesting Officer

C. MARSHALL DANN
Commissioner of Patents and Trademarks